United States Patent [19]

Bhattacharya et al.

[11] Patent Number: 5,116,983
[45] Date of Patent: May 26, 1992

[54] DEHYDROGENATION PROCESS INTERMEDIATES

[75] Inventors: Apurba Bhattacharya, Rahway; Alan W. Douglas, Monmouth Junction; Edward J. Grabowski; Ulf H. Dolling, both of Westfield, all of N.J.

[73] Assignee: Merck & Co., Inc., Rahway, N.J.

[21] Appl. No.: 520,991

[22] Filed: May 8, 1990

Related U.S. Application Data

[63] Continuation of Ser. No. 182,806, Apr. 18, 1988, abandoned.

[51] Int. Cl.$^5$ ................................................. C07F 7/04
[52] U.S. Cl. .......................................... 546/14; 546/77; 546/78
[58] Field of Search ............................... 546/14, 77, 78

[56] References Cited

U.S. PATENT DOCUMENTS

| | | | |
|---|---|---|---|
| 4,036,831 | 7/1977 | Loken et al. | 260/239.55 D |
| 4,220,775 | 9/1980 | Rasmussen et al. | 546/77 |
| 4,377,584 | 3/1983 | Rasmussen et al. | 546/77 |

FOREIGN PATENT DOCUMENTS

| | | | |
|---|---|---|---|
| EPA0004949 | 10/1979 | European Pat. Off. | 546/14 |
| 0155096 | 9/1985 | European Pat. Off. | 546/77 |
| 1805857 | 6/1969 | Fed. Rep. of Germany | 546/14 |

OTHER PUBLICATIONS

Patpharma Establishment, *Chem. Abstracts* 94: Abs.#103680s, 103681t, 103682u, 103683v, 103684w: 779–780 (1981).
*J. Am. Chem. Soc.* 110: Bhattacharya, et al., 3318–3319 (1988).
Back, T. G., *J. Org. Chem.* 46: 1442 (1981).
Rasmussen et al., *J. Med. Chem.* 29: 2298 (1986).
Magnus et al., *J. Am. Chem. Soc.* 108: 221–227 (1986).

*Primary Examiner*—Robert T. Bond
*Attorney, Agent, or Firm*—Robert J. North; Charles M. Caruso

[57] ABSTRACT

A process for dehydrogenating a compound of the formula

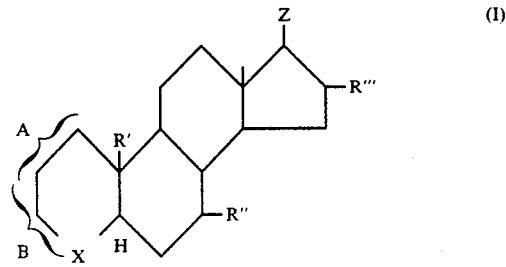

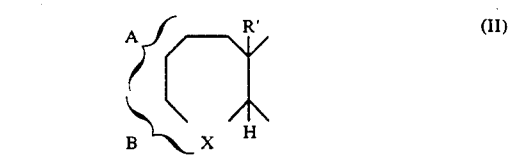

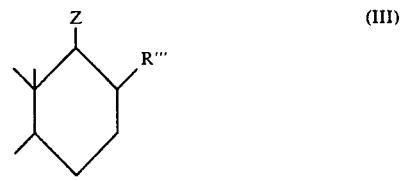

which comprises reacting the compound with a silylating agent in the presence of a quinone to introduce a $\Delta^1$ double bond.

6 Claims, No Drawings

DEHYDROGENATION PROCESS INTERMEDIATES

This is a continuation of application Ser. No. 07/182,806, filed Apr. 18, 1988, now abandoned.

BACKGROUND OF THE INVENTION

The present invention is concerned with a process for dehydrogenating compounds, particularly 3-oxo-4 azasteroids, to prepare corresponding $\Delta^1$ compounds and novel intermediates utilized in the process.

Heretofore, azasteroids have been dehydrogenated to introduce a $\Delta^1$ double bond by means of benzene seleninic anhydride oxidation in which the saturated compound was heated with the benzene seleninic anhydride in refluxing chlorobenzene. Back, T. G., J. Org. Chem. 46: 1442 (1981); Rasmussen et al., J. Med. Chem. 29: 2298 (1986). Additionally, sulfoxide elimination has been a process used to accomplish the dehydrogenation. See U.S. Pat. No. 4,377,584, 4,220,775 and EP application 85301122.9 (published Sep. 18, 1985). However, these reactions have been found to give poor yields, with a high degree of impurities and one requires the use of a selenium catalyst which is very expensive and is quite toxic.

It has also been known to dehydrogenate a 3-oxo-4-azalactam by a complicated 5-step process which involves a sulfenate intermediate. See Magnus et al., J. Am. Chem. Soc. 1986: 108 221-227. However, the process of the present invention provides a versatile single-pot process for the direct introduction of a $\Delta^1$ double bond into 3-oxo 4-azasteroids in high yields and without the attendant toxicity and impurity problems associated with the prior art.

The process of the present invention is a single pot silyation mediated quinone oxidation of lactams, lactones and 3-keto 4 azasteroids to the corresponding $\Delta^1$ double bond compound. The present invention provides a unique way to dehydrogenate a wide variety of compounds while avoiding the disadvantages of the prior art methods of effecting such transformations. The disadvantages overcome by the present invention include complicated multi step processes, poor yields, unwanted by-products and the us of toxic selenium catalysts.

SUMMARY OF THE INVENTION

The present invention provides a process for dehydrogenating a compound of the formula

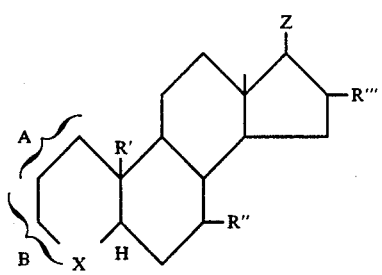

(I)

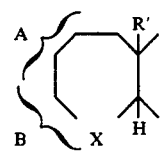

(II)

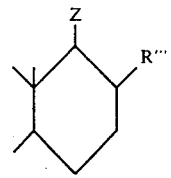

(III)

where Formula (I) may alternatively have the structure of partial Formulas (II) and/or (III); wherein, A is (1) $-CH_2-CH_2-$;

(2) $-\underset{1}{CH}-\underset{2}{CH_2}-$;  (with $CH_3$ on position 1)

B is (1)

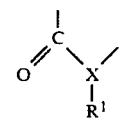

where
X is N, O or $CH_2$; and
$R^1$ is absent or is
(a) hydrogen;
(b) methyl or ethyl;
(c) $NR^2R^3$ where $R^2$ and $R^3$ are hydrogen or methyl; or
(d) cyano; or (2)

(a) 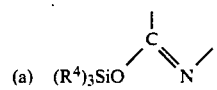

(b) 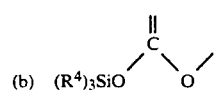

(c) 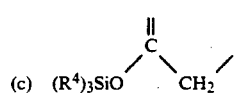

(d) 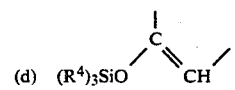

(e) 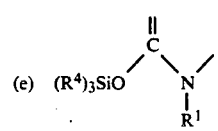

where $R^4$ is any of methyl, $C_{1-8}$ straight or branched chain alkyl, $C_{3-6}$ cycloalkyl, phenyl or combinations thereof;
$R'$ is hydrogen or methyl;
$R''$ is hydrogen or $\beta$-methyl;

R''' is hydrogen, β-methyl or hydroxyl;
Z is
(1) β-hydroqen and α-hydroxyl;
(2) α-hydrogen or α-hydroxyl and
(a)

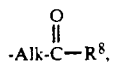

where Alk is present or absent and is a straight or branched hydrocarbon chain of 1 to 12 carbon atoms; and $R^8$ is,
(i) hydrogen,
(ii) hydroxyl,
(iii) $C_{1-12}$ alkyl,
(iv) $NR^9R^{10}$, where $R^9$ and $R^{10}$ are each independently selected from hydrogen; $C_{1-12}$ straight or branched chain alkyl; $C_{1-12}$ straight or branched chain alkyl having a hydrogen substituted with a hydroxy, carboxylic acid or $C_{1-4}$ alkyl ester; $C_{1-6}$ cycloalkyl; phenyl; or $R^9$ and $R^{10}$ taken together with the nitrogen to which they are attached represent a 5-6 membered saturated ring comprising up to one other heteroatom selected from oxygen and nitrogen; or
(v) $OR^{11}$, where $R^{11}$ is M, where M is hydrogen or alkali metal, or $C_{1-18}$ straight or branched chain alkyl; benzyl; or
(b) —(Alk)—$OR^{12}$, where Alk is present or absent and has the same meaning as above; and $R^{12}$ is
(i) phenyl $C_{1-6}$ alkylcarbonyl,
(ii) $C_{5-10}$ cycloalkylcarbonyl,
(iii) benzoyl, or
(iv) $C_{1-18}$ alkoxycarbonyl;
(v) hydrogen;
(3)

or=CH—Alk—$OR^{12}$, where Alk is present or absent and has the same meaning as above, and $R^8$ and $R^{12}$ have the same meaning as above, and $R^{12}$ is also hydrogen or $C_{1-20}$ alkylcarbonyl;
(4)

where the dashed bond replaces the 17α hydrogen;
(5) α-hydrogen and

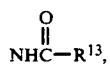

where $R^{13}$ is,
(a) $C_{1-12}$ alkyl; or
(b) $NR^9R^{10}$;
(6) α-hydrogen and cyano; or
(7) α-hydrogen and tetrazolyl;
which comprises reacting the compound with a silylating agent in the presence of a quinone to introduce a $\Delta^1$ double bond.

The azasteroid compounds prepared by the processes of the present invention are testosterone5α-reductase inhibitors useful for treating the hyperandrogenic conditions of acne vulgaris, seborrhea, female hirsutism, androgenic alopecia including male pattern alopecia, prostatic carcinoma and benign prostatic hypertrophy by topical or systemic administration.

Novel silylated intermediate compounds useful in preparing the corresponding $\Delta^1$ compound are also an important part of the present invention.

DETAILED DESCRIPTION OF THE INVENTION

Generally, the process of the invention involves treatment of the saturated starting lactam, lactone or azasteroid with a silyating agent in the presence of a quinone. A number of silylating agents capable of sily lactams, lactones and azasteroids can be used. For example, bistrimethylsilylacetamide, bistrimethylsilyltrihaloacetamide, hexamethyldisilazane or bistrimethylsilylurea are silyating agents that can be used in the processes of the present invention. The bistrimethylsilyltrihaloacetamide silyating agent can have any halo group as a moiety thereof, such as chloro, fluoro, bromo or iodo. The preferred silyating agent is bistrimethylsilyltrifluoroacetamide (BSTFA).

Primarily, the readily available 2,3 dichloro-5,6-dicyano 1,4-benzoquinone (DDQ) and 3,4,5,6-tetrachloro-1,2-benzoquinone are preferred for use in the process of the present invention, but any other quinone of sufficient reaction potential can also be used. For example, ortho- or para-benzoquinones of the following formula:

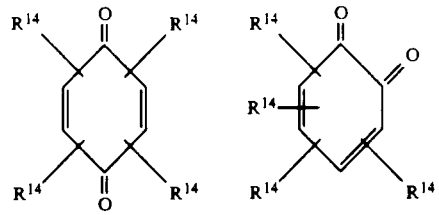

where $R^{14}$ is hydrogen, $C_{1-6}$ alkyl, $C_{1-6}$ alkoxy, halo such as Cl, F, I, Br, nitro or cyano, can be used in the present invention. This would include quinones such as 2,3,5-trimethyl-1,4 benzoquinone, 2,6-dimethyl-1,4-benzoquinone, 2,6-di-t-butyl-1, 4-benzoquinone, 3,5-di-t-butyl-1,2-benzoquinone and 2,3 di-alkoxy-1,4 benzo quinone. Other quinones of sufficient reaction potential can be substituted for DDQ and still be within the scope of the present invention.

As a general procedure, a lactam, lactone or 3-keto-4-azasteroid is treated with a quinone and a silyating agent in aliphatic or cyclic ethers, or chlorinated or aromatic hydrocarbon solvents with or without strong acid actalysis and with or without preliminary low temperature aging and then, first at a lower temperature, and then at elevated temperatures under nitrogen for 5 to 25 hours to cleanly produce the corresponding dehydrogenated lactam, or lactone in high yield. These conditions were also used to convert a 3-keto-4-azasteroid to the corresponding $\Delta^1$-azasteroid with consistently high yields.

The reaction scheme can be represented as follows:

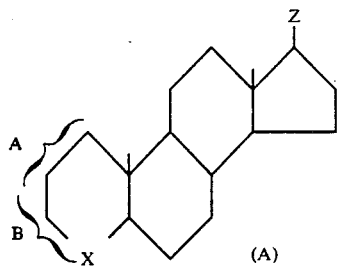

(A)

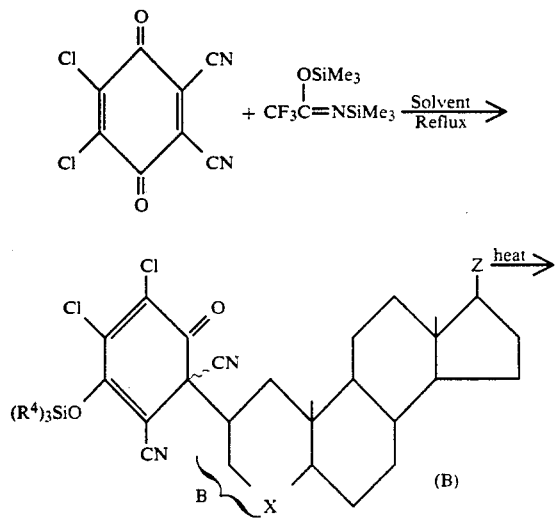

(B)

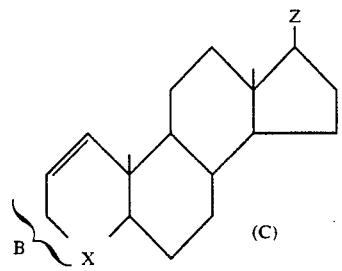

(C)

When X is NR[1], O or CH$_2$, the compound of A is reacted with DDQ and BSTFA to form a diastereomeric intermediate B of the following partial structure:

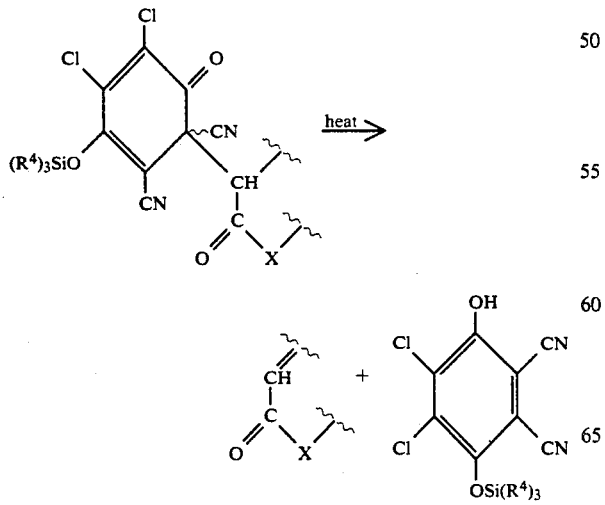

X = NR[1], O or CH$_2$

Heating the diastereomeric mixture B results in formation of the corresponding $\Delta^1$ compound. Cyclohexane-1,3-dione is used to decompose the residual DDQ prior to thermolysis.

When X is N or CH$_2$, the compound A is reacted with DDQ and BSTFA to form an intermediate according to the following partial structure:

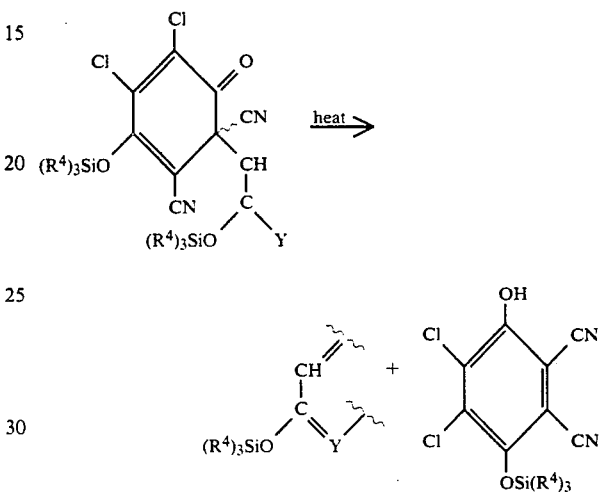

Y = N, CH$_2$

For example, the 17β-carboxy-4-aza-androstan--3-one (A) is reacted with dichlorodicyano-p-benzoquinone (DDQ) and bistrimethyl-silyltrifluoro-acetamide (BSTFA) to form a diastereomeric intermediate (B). The intermediate (B) is subjected to dioxane reflux under heat to form the 17β-carboxy-3-oxo-4-substituted-4-aza-androst-1-ene-3-one (C) corresponding to formula I.

The novel chemical intermediates formed in the process disclosed herein is also a significant part of the present invention. These novel chemical intermediates (B) are formed as diastereomeric mixtures, however, each diastereomer is included within the scope of the invention. The intermediates are compounds of the formula:

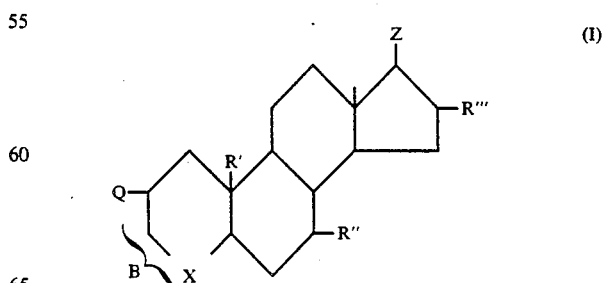

(I)

wherein:
Q is absent or is

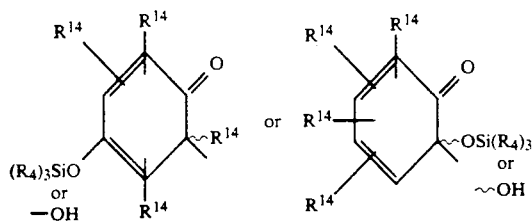

where $R^4$ is methyl, $C_{1-8}$ straight or branched chain alkyl, $C_{3-6}$ cycloalkyl, phenyl, or combinations thereof; and $R^{14}$ is hydrogen, $C_{1-6}$ straight or branched alkyl, $C_{1-6}$ alkoxy, halo, nitro or cyano;

B is (a) when Q is present,

where X is $NR^1$, O or $CH_2$; and $R^1$ is absent or is hydrogen, methyl or ethyl;

(b)

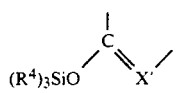

where X' is N or CH;

(c)

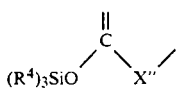

where X" is O or $CH_2$;

Z is (1) β-hydrogen and α-hydroxyl;
(2) α-hydrogen or α-hydroxyl and (a)

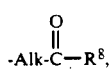

where Alk is present or absent and is a straight or branched hydrocarbon chain of 1 to 12 carbon atoms; and $R^8$ is, (i) hydroqen,
(ii) hydroxyl,
(iii) $C_{1-12}$ alkyl
(iv) $NR^9R^{10}$, where $R^9$ and $R^{10}$ are each independently selected from hydrogen; $C_{1-12}$ straight or branched chain alkyl; $C_{1-12}$ straight or branched chain alkyl having a hydroqen substituted with a hydroxy, carboxylic acid or $C_{1-4}$ alkyl ester; $C_{3-6}$ cycloalkyl; phenyl; or $R^9$ and $R^{10}$ taken together with the nitrogen to which they are attached represent a 5–6 membered saturated ring comprising up to one other heteroatom selected from oxygen and nitrogen; or
(v) $OR^{11}$, where is M, where M is hydrogen or alkali metal, or $C_{1-18}$ straight or branched chain alkyl; benzyl; or (b) —(Alk)—$OR^{12}$, where Alk is always present and has the same meaning as above; and $R^{12}$ is (i) phenyl $C_{1-6}$ alkylcarbonyl,
(ii) $C_{5-10}$ cycloalkylcarbonyl,
(iii) benzoyl, or
(iv) $C_{1-18}$ alkoxycarbonyl;
(v) amino, or $C_{1-8}$ alkyl substituted amino, carbonyl; or
(vi) hydrogen, provided that Alk is a branched $C_{3-8}$ chain;

(3)

or=CH—Alk—$OR^{12}$, where Alk is present or absent and has the same meaning as above, and $R^8$ and $R^{12}$ have the same meaning as above, and $R^{12}$ is also hydroqen or $C_{1-20}$ alkylcarbonyl;

(4)

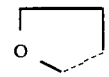

where the dashed bond replaces the 17α hydrogen;

(5) α-hydrogen and

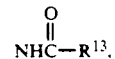

where $R^{13}$ is, (a) $C_{1-12}$ alkyl; or
(b) $NR^9R^{10}$;
(6) α-hydrogen and cyano; or
(7) α-hydrogen and tetrazolyl;

R' is hydrogen or methyl;
R" is hydrogen or β-methyl;
R''' is hydrogen, β-methyl or hydroxyl.

The following examples should be considered as not limiting the invention and will serve to illustrate the manner in which the present invention is accomplished.

EXAMPLE 1

3-Oxo-4 aza-5α-androst-1 ene-17β-carboxylic acid

A 1 l three neck round bottom flask equipped with a nitrogen inlet, reflux condenser, addition funnel, mechanical stirrer and an immersion thermometer was charged with 180 mL dioxane followed by 18 g of 3 oxo-4-aza 5α-androstan-17β-carboxylic acid portionwise with stirring. To the stirred suspension was added portionwise 13.86 g of DDQ. The flask was evacuated (22" Hg) and flushed with nitrogen three times. To this stirred suspension was added BSTFA via the addition funnel at the rate of 50 mL/minute. The temperature slowly went up form 22° to 25° in a period of thirty minutes as most of the solids dissolved within this period to afford a clear solution.

The solution was stirred for 18 hours at 22° after which time formation of the two diastereomeric adducts were observed.

To the solution was added 0.54 g cyclohexane-1,3-dione and the reaction mixture was stirred at 22° for an additional three hours to decompose any residual DDQ.

The solution was then heated in an oil bath so that a very gentle reflux was maintained. (Bath temperature 120°, Internal Temperature 108°) After refluxing for 20 hours complete disappearance of the adducts and formation of $\Delta^1$ acid were observed.

The reaction mixture was cooled to 22° and poured slowly over a period of 2 minutes into a stirred mixture of 300 mL $CH_2Cl_2$ and 60 mL 1% aqueous sodium bisulfite solution.

The flask was rinsed with 50 mL $CH_2Cl_2$. After the mixture was stirred for thirty minutes, 18 mL 6N HCl was added to this mixture and stirred for an additional thirty minutes. The heterogeneous mixture was filtered and the residue was washed with 60 mL 1N HCl followed by 250 mL $CH_2Cl_2$. The filtrated was transferred into a seperatory funnel and allowed to settle. The bottom $CH_2Cl_2$ layer containing the product was separated from the top aqueous layer and the top layer was washed with 60 mL $CH_2Cl_2$. The combined $CH_2Cl_2$ layer was washed with 200 mL 2N HCl. The aqueous layer was washed with 60 mL $CH_2Cl_2$. The two $CH_2Cl_2$ solutions were combined. The liquid chromatography yield at this stage was 16.0 g (88%). The combined $CH_2Cl_2$ solution was then distilled and concentrated to about 120 mL volume. The distillation was continued and acetonitrile was added to the flask at such a rate so that the total volume was maintained at approximately 120 mL. After addition of about 400 mL acetonitrile the distillation head showed a temperature of about 82°. Gas chromatography analysis performed on the mother liquor showed the presence of about 2% dioxane. The distillation was discontinued at this point. The suspension was cooled to 20° and aged at 20° for 20 hours with stirring. The crystals were filtered and washed with acetonitrile until the filtrate was colorless. Approximately 100 mL acetonitrile was used for the wash. The wet cake was dried at 60° C. under vacuum (about 1 mm μg) overnight to produce 15.3 g of the $\Delta^1$ acid.

EXAMPLE 2

17β-(t butylcarbamoyl)-4-aza 5α-androst-1-ene-3-one

A 50 ml three neck round bottom flask equipped with a nitrogen inlet, reflux condenser, addition funnel, magnetic stirrer and an immersion thermometer was charged with 10 ml dioxane followed by 1 g of 17β-N (t-butylcarbamoyl)-4-aza-5α-androstan-3-one portionwise with stirring. To the stirred suspension was added portionwise 0.656 g DDQ. The flask was evacuated (20" Hg) and flushed with nitrogen three times. To this stirred suspension was added BSTFA via a syringe at the rate of about 2 mL/min. Most of the solids dissolved during a period of half of an hour to afford a clear red solution. The solution was stirred for 18 hours at 22° after which time complete disappearance of standing material and formation of the two diastereometric adducts were observed by liquid chromatography. To this solution was added cyclohexane 1,3-dione and the reaction mixture was stirred at 22° for an additional three hours to decompose any residual DDQ. The solution was then heated in an oil bath so that a very gentle reflux was maintained. After refluxing for 20 hours complete disappearance of the adducts and formation of the title compound were observed by liquid chromatography. The reaction mixture was cooled to 22° and poured slowly into a stirred mixture of 30 ml CH and 6 mL 1% aqueous sodium bisulfite solution. The flask was rinsed with 10 mL $CH_2Cl_2$. After the mixture was stirred for 15 minutes 4 mL 6N HCl was added to this mixture and stirred for an additional 15 minutes. The heterogeneous mixture was filtered and the residue was washed with 20 mL $CH_2Cl_2$. The filtrate was transferred to a seperatory funnel and allowed to settle. The bottom $CH_2Cl_2$ layer containing the product was separated from the top aqueous layer and the top layer was washed with 20 mL $CH_2Cl_2$. The combined $CH_2Cl_2$ layer was washed with 20 mL 2% sodium hydroxide solution. The $CH_2Cl_2$ solution was then distilled and concentrated to about 6 mL volume. The distillation was continued and isopropyl acetate was added to the flask at such a rate so that the total volume was maintained at approximately 6 mL. The distillation was discontinued when the distillation head showed a temperature of about 85°. The suspension was cooled at 0° for 6 hours. The crytals were filtered and washed with 2 mL isopropyl acetate. The crystals were dried at 60° under vacuum (1 mr Hg) overnight to produce 0.8 g of the title compound (80%).

EXAMPLE 3

To 250 mg of 17-β-(t butylcarbamoyl)-4-aza-5α-androstan-3-one in a glass NMR tube were added approximately 2 mL of methylene chloride (as a $CH_2Cl_2CD_2Cl_2$ mixture suitable for NMR studies), 0.7 mL BSTFA and 60 mcL $CF_3SO_3H$. The tube was cooled in methanol-ice and 168 mg tetrachloro-1,2-benzoquinone added accompanied by injection of a stream of dry $N_2$. The tube was then closed with a snugly fitting polyethylene stopper, sealed with stretched Parafilm ®, agitated briefly with only momentary warming, and placed in a cooled NMR probe which had been previously adjusted for $^{13}C$ observations of reaction intermediates at approximately −5° C. Spectra were obtained from time to time over a period of two days during which the sample temperature was maintained between zero and −10° C. The solution was then allowed to age five days at ambient temperature while additional spectra were recorded from time to time. At the end of this aging the entire solution was quantitatively transferred, quenched with 1 mL acetic acid and volumetrically diluted for replicate HPLC analyses which gave 80–84% yield, based on assay vs pure 17β-(t-butylcarbamoyl)-4-aza-5α-androst-1-ene-3-one, from the saturated lactam precursor.

EXAMPLE 4

A 100 mL three-neck round bottom flask equipped with a nitrogen inlet, reflux condenser, magnetic stirrer and a septum inlet was charged with 17-β-(t-butylcarbamoyl)-4-aza-5α-androstan-3-one (4.0 g), DDQ (4.0 g) and dioxane (26 ml). To this suspension was added BSTFA (10.5 g) with stirring via a syringe over a period of 1 min. Heating the mixture at reflux for 10 minutes afforded a clear solution. The solution was refluxed for 18 hours at the end of which complete disappearance of starting material was observed by LC. The solution was cooled to room temperature and added to a mixture of 100 mL each 5% $NaHSO_3$ and $CH_2Cl_2$, precipitating the hydroquinone which was separated by filtration. The $CH_2Cl_2$ layer of the filtrate was separated, extracted twice with 100 mL of 5% $NaHSO_3$, concentrated to a thick oil and triturated with 200 mL diethyl ether. First and second crop solids were isolated and dried 4 hours at 50° under vacuum yielding a total of 3.28 g of 88% pure 17-β-(t-butylcarbamoyl)-4-aza-5α-androst-1ene-3-one.

EXAMPLE 5

3-Oxo-4-aza-5α-androst-1-ene 17β-carboxylic acid ($\Delta^1$-Aza acid)

A 1 L 3-neck round bottom flask equipped with a nitrogen inlet, reflux condenser, additional funnel, mechanical stirrer and an immersion thermometer was charged with 320 mL of toluene, 20 g of 3-oxo-4-aza-5α-androstan-17β-carboxylic acid, 5.7 g of DDQ, 70 mL of BSTFA and 0.32 mL of triflic acid. The flask was evacuated and flushed with $N_2$ three times. The reaction mixture was stirred for 18 h at 38°–40° after which time complete disappearance of starting material and formation of two diastereomeric adducts was observed by LC. Cyclohexane 1,3-dione (0.8 g) was added and the reaction mixture was stirred at 38°–40° for 3 hours to quench any residual DDQ. The solution was then heated to gentle reflux for 20 h after which time complete disappearance of the adducts and formation of the $\Delta^1$-acid (95% assay yield) was observed by LC. The reaction was cooled to 20° C. Aqueous NaOH (430 mL, 1% by wt) and 20 mL of isopropanol were added. The mixture was stirred for 30 min, allowed to settle and the bottom aqueous layer was re extracted with a mixture of 430 mL toluene and 120 mL i-propanol. The combined toluene layers were extracted with 320 mL of 1% NaOH. The bottom aqueous layer containing the product was extracted and the organic layer was washed with another 160 mL of 1% NaOH. The aqueous layers were combined and isopropanol removed by vacuum distillation and replaced with 100 mL of acetonitrile. The mixture was warmed to 60°–65° C. and acidified with 12 mL of 6N HCl to pH 1, aged at 60°–65° C. for 2 hours, cooled to 20° C. and aged for 18 hours and filtered. The filter cake was washed with 100 mL of $H_2O/CH_3CN$ (4/1). The product was dried at 50°–60° C. under vacuum to yield 17.6 g (88%) of the desired $\Delta^1$-aza acid.

EXAMPLE 6

Methyl-3-oxo-4-aza-5α-androst-1-ene-17β-carboxylate

A 1 L three-neck round bottom flask equipped with a nitrogen inlet, reflux condenser, additional funnel, mechanical stirrer and an immersion thermometer was charged with 320 mL of toluene, 20 g of methyl-3 oxo 4-aza 5α-androstan 17β-carboxylate, 14.73 g of DDQ, 67 mL of BSTFA and 0.32 mL triflic acid. The flask was evacuated and flushed with $N_2$ three times. The reaction mixture was stirred for 18 h at 22° after which time complete disappearance of starting material and formation of the two diastereomeric adducts was observed by LC. Cyclohexane 1,3-dione was added and the reaction mixture was stirred at 22° for 3 hours to quench any residual DDQ. The solution was then heated to gentle reflux for 20 h after which time complete disappearance of the adducts and formation of the methyl 3-oxo-4-aza-5 -androst-1-ene-17-carboxylate was observed by LC. The toluene solution was cooled to 22° C. and 42 mL $CH_2Cl_2$ and 390 mL saturated sodium bicarbonate solution added with stirring. The bottom layer was separated from the top organic layer containing the product. The top layer was washed once more with 390 mL saturated sodium bicarbonate solution. The toluene solution was distilled to 100 mL volume. Toluene was displaced by n Butylacetate via distillation maintaining 100 mL volume. The slurry was aged at 22° for 18 hours and filtered to produce the product steroid in 91% yield.

EXAMPLE 7

By following the procedure of the preceding example a 90% yield of 17β-(t-butylcarbamoyl)-4-aza-5α-androst-1-ene-3-one was obtained from the corresponding 17β-(t-butylcarbamoyl)-4-aza-5-α-androstan-3-one.

EXAMPLE 8

By following the procedure of the preceeding example a 90% yield of 22(R,S)-methyl-4-aza-21-nor-5α-cholen-3,20 dione was obtained from the corresponding 22(R,S)-methyl-4-aza-21-nor-5α-cholan-3,20-dione.

EXAMPLE 9

A 100 mL three neck round bottom flask equipped for magnetic stirring and a nitrogen inlet was charged with 2 g of 17β-(t-butylcarbamoyl)-4-aza-5α-androstan-3-one, 20 mL $CH_2Cl_2$, and 1.344 g of ortho chloranil. The solution was cooled to −8° by means of methanol-/ice cooling and 6 mL BSTFA was added via syringe (ca. 1 min) followed by 0.48 mL triflic acid. The solution was stirred at −10° for 2 days followed by 22° for 6 days, after which time complete disappearance of starting material was observed by LC. At the end of this age HPLC analyses showed 1.6 g of 17β-(t-butylcarbamoyl)-4-aza-5α-androst-1-ene-3-one (based on assay vs pure 17β-(t-butylcarbamoyl)-4-aza-5α-androst-1-ene-3-one; yield 80%.

EXAMPLE 10

Isolation of the diastereomeric adduct formed between 3-oxo-4-aza-5α-androstan-17β-carboxylic acid and DDQ A 100 mL 3 neck round bottom flask equipped with a nitrogen inlet and magnetic stirring was charged with 20 mL tetrahydropyran, 2 g of 3-oxo-4-aza-5α-androstan-17β-carboxylic acid, 6.7 mL of BSTFA, 1.47 g of DDQ and 2 mcL of triflic acid. The solution was stirrd under $N_2$ for 20 hours at 22° after which time complete disappearance of starting material and formation of the two diastereomeric adducts was observed by LC. The solution was cooled to 4° (ice cooling) and 0.2 mL water was added to it. The mixture was stirred at 4° for 3 hours. The solvent was removed at 20° in the rotovapor to afford a yellow oil which was tritiated with 60 mL $CH_2Cl_2$. The two diastereomeric adduct crystallized. The crystals were aged for 1 hour at 22° filtered, washed with 20 mL $CH_2Cl_2$ and dried in vacuum at 22° to afford 90% yield of the two diastereomeric adducts.

EXAMPLE 11

Preparation of 3-oxo-4-aza-5α-androst-1-ene-17β-carboxylic acid via thermolysis of the isolated diasteremeric adducts 100 mg of the two diasteromeric adducts (obtained in Example 10) were heated in 2 mL dioxane under $N_2$ atmosphere for 18 hours to produce 36 mg (by LC analysis, 60%) of the desired 3-oxo-4-aza-5α-androst-1-ene-17β-carboxylic acid.

EXAMPLES 12-37

By following the procedures of Example 1 or 2 but substituting the corresponding 1,2-saturated steroid as a starting material, the following compounds could be obtained.

| Example | Compound Name |
|---|---|
| 12 | 17β-hydroxy-4-aza-5α-androst-1-en-3-one |
| 13 | 3-oxo-4-aza-5α-pregn-1-ene-20α-carboxylic acid |
| 14 | methyl-3-oxo-4-aza-5α-pregn-1-ene-20α-carboxylate |
| 15 | 2′,3′α-tetrahydrofuran-2′-spiro-17-(4-aza-5α-androst-1-en-3-one) |
| 16 | 23-methyl-4-aza-21-nor-5α-chol-1-ene-3,20-dione |
| 17 | 17β-(2-pyrrylcarbonyl)-4-aza-5α-androst-1-en-3-one |
| 18 | 17β-(t-butyldimethylsilyloxy)-4-aza-5α-androst-1-en-3-one |
| 19 | 3-oxo-4-aza-5α-androst-1-ene-17β-carboxamide |
| 20 | N-ethyl-3-oxo-4-aza 5α-androst-1-ene-17β-carboxamide |
| 21 | N-(2,4,4,-trimethyl-2-pentyl) 3-oxo-4-aza-5α-androst-1-ene-17β-carboxamide |
| 22 | N,N-bis(2-propyl) 3-oxo-4-aza-5α-androst-1-ene-17β-carboxamide |
| 23 | 17β-hydroxy-4-methyl-4-aza-5α-androst-1-en-3-one |
| 24 | 4-methyl-3-oxo-4-aza-5α-pregn-1-ene-20α-carboxylic acid |
| 25 | methyl-4-methyl-3-oxo-4-aza-5α-pregn-1-20α-carboxylate |
| 26 | 2′,3′α-tetrahydrofuran-2′-spiro-17-(4-methyl-4-aza-5α-androst-1-en-3-one) |
| 27 | 4.23-dimethyl-4-aza-21-nor-5α-chol-1-ene-3,20-dione |
| 28 | 4,22-dimethyl-4-aza-21-nor-5α-chol-1-ene-3,20-dione |
| 29 | 4-methyl-17β-(2-pyrrylcarbonyl)-4-aza-5α-androst-1-en-3-one |
| 30 | 17β-(t-butyldimethylsilyloxy)-4-methyl-4-aza-5α-androst-1-en-3-one |
| 31 | methyl 4-methyl-3-oxo-4-aza-5α-androst-1-ene-17β-carboxylate |
| 32 | 4-methyl-3-oxo-4-aza-5α-androst-1-ene-17β-carboxamide |
| 33 | N-ethyl 4-methyl-3-oxo-4-aza-5α-androst-1-ene-17β-carboxamide |
| 34 | N-(t-butyl) 4-methyl-3-oxo-4-aza-5α-androst-1-ene-17β-carboxamide |
| 35 | N-octyl 4-methyl-3-oxo-4-aza-5α-androst-1-ene-17β-carboxamide |
| 36 | N-(2,4,4-trimethyl-2-pentyl) 4-methyl-3-oxo-4-aza-5α-androst-1-ene-17β-carboxamide |
| 37 | N,N-bis(2-propyl) 4-methyl-3-oxo-4-aza-5α-androst-1-ene-17β-carboxamide |

What is claimed is:

1. The compounds of the formula

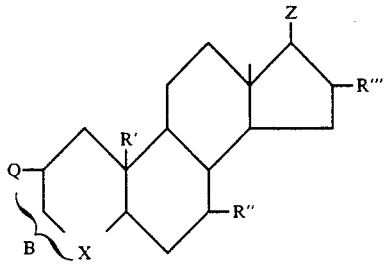

wherein:

Q is absent or is

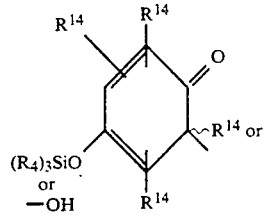

where $R^4$ is methyl, $C_{1-8}$ straight or branched chain alkyl, $C_{3-6}$ cycloalkyl, phenyl, or combinations thereof; and $R^{14}$ is hydrogen, $C_{1-6}$ alkyl, $C_{1-6}$ straight or branched chain alkoxy, halo, nitro or cyano;

B is (a) when Q is present,.

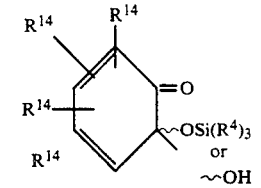

where X is $NR^1$; and $R^1$ is hydrogen; methyl or ethyl;

(b) when Q is absent,

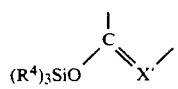

where X' is N;

(c)

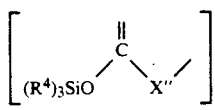

Z is
(1) β-hydrogen and α-hydroxyl;
(2) α-hydrogen or α-hydroxyl and
(a)

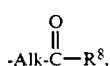

where Alk is present or absent and is a straight or branched hydrocarbon chain of 1 to 12 carbon atoms; and $R^8$ is,
(i) hydrogen,
(ii) hydroxyl,
(iii) $C_{1-12}$ alkyl
(iv) $NR^9R^{10}$, where $R^9$ and $R^{10}$ are each independently selected from hydrogen; $C_{1-12}$ straight or branched chain alkyl; $C_{1-12}$ straight or branched chain alkyl having a hydrogen substituted with a hydroxy, carboxylic acid or $C_{1-4}$ alkyl ester; $C_{3-6}$ cycloalkyl; phenyl; or $R^9$ and $R^{10}$ taken together with the nitrogen to which they are attached represent a 5-6 membered saturated ring comprising up to one other hereroatom selected from oxygen and nitrogen; or
(v) $OR^{11}$, where $R^{11}$ is M, where M is hydrogen or alkali metal, or $C_{1-18}$ straight or branched chain alkyl; benzyl; or
(b) —(Alk)—$OR^{12}$, where Alk is always present and has the same meaning as above; and $R^{12}$ is
(i) phenyl $C_{1-6}$ alkylcarbonyl,
(ii) $C_{5-10}$ cycloalkylcarbonyl,
(iii) benzoyl, or
(iv) $C_{1-18}$ alkoxycarbonyl;
(v) amino, or $C_{1-8}$ alkyl substituted amino, carbonyl; or
(vi) hydrogen, provided that Alk is a branched $C_3-C_8$ chain;
(3)

or=CH—Alk—$OR^{12}$, where Alk is present or absent and has the same meaning as above, and $R^8$ and $R^{12}$ have the same meaning as above, and $R^{12}$ is also hydrogen or $C_{1-10}$ alkylcarbonyl;
(4)

where the dashed bond replaces the 17α hydrogen;
(5) α-hydrogen and

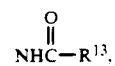

where $R^{13}$ is,
(a) $C_{1-12}$ alkyl; or
(b) $NR^9R^{10}$;
(6) α-hydrogen and cyano; or
(7) α-hydrogen and tetrazolyl;
R' is hydrogen or methyl;
R'' is hydrogen or β-methyl;
R''' is hydrogen, β-methyl or hydroxyl.

2. The compounds of claim 1, wherein
Q is present and $R^4$ is methyl;
B is

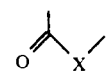

where X is $NR^1$;
R'', R''' are hydrogen;
Z is

where $R^8$ is
(i) —$NHC_{3-12}$ branched alkyl;
(ii) —$NHC_{3-12}$ branched alkyl having a hydrogen substituted with a hydroxy, carboxylic acid or $C_{1-4}$ alkyl ester;
(iii) —$C_{3-12}$ branched alkyl; or
(iv) —$OCH_3$.

3. The compounds of claim 2 wherein
$R^8$ is —NH-t-butyl,

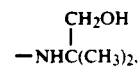

sec-butyl, isobutyl or —$OCH_3$.

4. The compound of claim 3 wherein $R^1$ is hydrogen and $R^8$ is —NH-t-butyl.

5. The compound of claim 4 where Q is

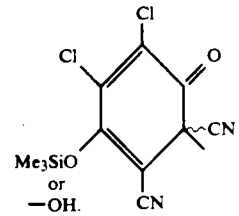

6. The compound of claim 4 where Q is

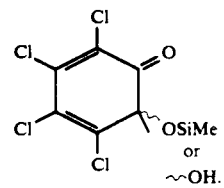

* * * * *